United States Patent [19]
Ishizuka et al.

[11] Patent Number: 5,888,766
[45] Date of Patent: Mar. 30, 1999

[54] METHOD FOR PRODUCING RECOMBINANT HUMAN MYOGLOBIN

[75] Inventors: Toshihiro Ishizuka; Yasunori Kihira; Toshio Tanaka, all of Shiga; Yushi Matuo, Osaka-fu, all of Japan

[73] Assignee: Oriental Yeast Co., Ltd., Tokyo, Japan

[21] Appl. No.: 536,941

[22] Filed: Sep. 29, 1995

[30] Foreign Application Priority Data

Oct. 7, 1994 [JP] Japan ..................................... 6-268121

[51] Int. Cl.$^6$ .............................. C12P 21/06; C12N 1/20; C07H 17/00; C07K 14/805
[52] U.S. Cl. .................................... 435/69.1; 435/252.33; 435/320.1; 536/23.5; 530/385
[58] Field of Search .............................. 435/69.01, 240.1, 435/320.1; 530/385, 350

[56] References Cited

PUBLICATIONS

Georgiou 1988 Alche J. 34(8): 1233–1248.
Spinger et al 1987 P.N.A.S. 84: 9861–8965.
Furman et al 1987 Bio/Technology 5:1047–1050.
Guillemette et al. 1991 Prot. Eng. 4(5):585–592.
Grojean 1982 Gene 18: 199–209.
Eiko Akaboshi, Cloning of the Human Mycoglobin Gene, Elsevier Publications, vol. 33, pp. 241–249, 1985.
Varadarajan et al, Cloning, Expression in *Escherichia coli*, and Reconstruction of Human Mycoglobin, Proc. Natl. Acad. Sci., vol. 82, pp. 5681–5684, Sep. 1985.

*Primary Examiner*—Karen Carlson
*Attorney, Agent, or Firm*—Browdy and Neimark

[57] ABSTRACT

The present invention relates to a method for producing human myoglobin by inserting a DNA sequence comprising a human myoglobin gene into a tryptophan promoter-containing vector, followed by making *E. coli* with the thus-obtained expression vector express a holo-type human myoglobin. Using this method, it is possible to directly and efficiently produce a heme-structured, holo-type human myoglobin by gene recombination technology.

11 Claims, 6 Drawing Sheets

FIG. 1

Fragment: F1(96mer), F2(95mer), F3(98mer), F4(98mer), F5(97mer), F6(101mer)

```
        1          11         21         31         41         51

F1  CCGAATTCAT GGGTCTGTCT GACGGTGAAT GGCAGCTGGT TCTGAACGTT TGGGGTAAAG
    GGCTTAAGTA CCCAGACAGA CTGCCACTTA CCGTCGACCA AGACTTGCAA ACCCCATTTC 61         71         81         91        101        111

TTGAAGCTGA CATCCCGGGT CATGGTCAGG AAGTTCTGAT CCGTCTGTTT AAAGGTCATC
    AACTTCGACT GTAGGGCCCA GTACCAGTCC TTCAAGACTA GGCAGACAAA TTTCCAGTAG
                    F2

121        131        141        151  F3    161        171

CGGAAACCCT GGAAAAGTTC GATAAATTTA AACATCTGAA ATCTGAAGAC GAAATGAAAG
    GCCTTTGGGA CCTTTTCAAG CTATTTAAAT TTGTAGACTT TAGACTTCTG CTTTACTTTC 181        191        201        211        221        231

CTTCTGAAGA CCTGAAAAAA CATGGTGCTA CCGTTCTGAC CGCTCTGGGT GGCATCCTGA
    GAAGACTTCT GGACTTTTTT GTACCACGAT GGCAAGACTG GCGAGACCCA CCGTAGGACT
                                                         F4

241        251        261        271        281        291

AAAAGAAAGG TCATCATGAA GCTGAAATCA AACCGCTGGC TCAGTCTCAT GCTACCAAAC
    TTTTCTTTCC AGTAGTACTT CGACTTTAGT TTGGCGACCG AGTCAGAGTA CGATGGTTTG

301   F5   311        321        331        341        351

ATAAAATCCC GGTTAAATAT CTGGAATTTA TCTCTGAATG CATCATCCAG GTTCTGCAGT
    TATTTTAGGG CCAATTTATA GACCTTAAAT AGAGACTTAC GTAGTAGGTC CAAGACGTCA 361        371        381        391        401        411

CTAAACATCC GGGTGACTTT GGTGCTGACG CTCAGGGTGC TATGAACAAA GCTCTGGAAC
    GATTTGTAGG CCCACTGAAA CCACGACTGC GAGTCCCACG ATACTTGTTT CGAGACCTTG
                                F6
      421        431        441        451        461        471

TGTTTCGTAA AGACATGGCT TCTAACTATA AGAACTGGG TTTTCAGGGT TGATAAGGAT
    ACAAAGCATT TCTGTACCGA AGATTGATAT TTCTTGACCC AAAAGTCCCA ACTATTCCTA

481

CCGG
    GGCC
```

```
  1  AGCGCCCAAT ACGCAAACCG CCTCTCCCCG CGCGTTGGCC GATTCATTAA TGCAGCTGGC
 61  ACGACAGGTT TCCCGACTGG AAAGCGGGCA GTGAGCGCAA CGCAATTAAT GTGAGTTAGC
121  TCACTCATTA GGCACCCCAG GCTTTACACT TTATGCTTCC GGCTCGTATG TTGTGTGGAA
181  TTGTGAGCGG ATAACAATTT CACACAGGAA ACAGCTATGA CCATGATTAC GCCAAGCTCT
                                              E.coli K12-DERIVED TRP PROMOTER
241  AATACGACTC ACTATAGGGA AAGCTT CCCTGTTGACAATTAATCATCGAACTAGTTAAC
                           HindIII
300  TAGTACGCAAGTTCACGTAAAAAGGGTA GAATTCGAGCTCGGTAGCCCGGGGATCCTCTAGA
                                    EcoRI                    BamHI
361  GTCGACCTGCAGGTCGAAATTC ACTGGCCG TCGTTTTACA ACGTCGTGAC TGGGAAAACC
              PstI
421  CTGGCGTTAC CCAACTTAAT CGCCTTGCAG CACATCCCCC TTTCGCCAGC TGGCGTAATA
481  GCGAAGAGGC CCGCACCGAT CGCCCTTCCC AACAGTTGCG CAGCCTGAAT GGCGAATGGG
541  ACGCGCCCTG TAGCGGCGCA TTAAGCGCGG CGGGTGTGGT GGTTACGCGC AGCGTGACCG
601  CTACACTTGC CAGCGCCCTA GCGCCCGCTC CTTTCGCTTT CTTCCCTTCC TTTCTCGCCA
661  CGTTCGCCGG CTTTCCCCGT CAAGCTCTAA ATCGGGGGCT CCCTTTAGGG TTCCGATTTA
721  GTGCTTTACG GCACCTCGAC CCCAAAAAAC TTGATTAGGG TGATGGTTCA CGTAGTGGGC
781  CATCGCCCTG ATAGACGGTT TTTCGCCCTT TGACGTTGGA GTCCACGTTC TTTAATAGTG
841  GACTCTTGTT CCAAACTGGA ACAACACTCA ACCCTATCTC GGTCTATTCT TTTGATTTAT
901  AAGGGATTTT GCCGATTTCG GCCTATTGGT TAAAAAATGA GCTGATTTAA CAAAAATTTA
961  ACGCGAATTT TAACAAAATA TTAACGTTTA CAATTTCAGG TGGCACTTTT CGGGAGAATG
1021 TGCCCGGAAC CCCTATTGT AATACATTC AAATATGTAT CCGCTCATGA
1081 GACATAACC CTGATAAATG ATTGAAAAAG GAAGAGTATG AGTATTCAAC
1141 ATTTCCGTGT CGCCCTTATT CCCTTTTTG CGGCATTTTG CCTTCCTGTT TTTGCTCACC
1201 CAGAAACGCT GGTGAAACTA AAAGATGCTG AAGATCAGTT GGGTGCACGA GTGGGTTACA
```

INITIATION CODON OF β-LACTAMASE

FIG. 4

```
1261 TCGAACTGGA TCTCAACAGC GGTAAGATCC TTGAGAGTTT TCGCCCCGAA GAACGTTTTC
1321 CAATGATGAG CACTTTTAAA GTTCTGCTAT GTGGCGCGGT ATTATCCCGT ATTGACGCCG
1381 GCCAAGAGCA ACTCGGTCGC CGCATACACT ATTCTCAGAA TGACTTGGTT GAGTACTCAC
1441 CAGTCACAGA AAAGCATCTT ACGGATGGCA TGACAGTAAG AGAATTATGC AGTGCTGCCA
1501 TAACCATGAG TGATAACACT GCGGCCAACT TACTTCTGAC AACGATCGGA GGACCGAAGG
1561 AGCTAACCGC TTTTTTGCAC AACATGGGGG ATCATGTAAC TCGCCTTGAT CGTTGGGAAC
1621 CGGAGCTGAA TGAAGCCATA CCAAACGACG AGCGTGACAC CACGATGCCT GTAGCAATGG
1681 CAACAACGTT GCGCAAACTA TTAACTGGCG AACTACTTAC TCTAGCTTCC CGGCAACAAT
1741 TAATAGACTG GATGGAGGCG GATAAAGTTG CAGGACCACT TCTGCGCTCG GCCCTTCCGG
1801 CTGGCTGGTT TATTGCTGAT AAATCTGGAG CCGGTGAGCG TGGGTCTCGC GGTATCATTG
1861 CAGCACTGGG GCCAGATGGT AAGCCCTCCC GTATCGTAGT TATCTACACG ACGGGAGTC
1921 AGGCAACTAT GGATGAACGA AATAGACAGA TCGCTGAGAT AGGTGCCTCA CTGATTAAGC
1981 ATTGG TAACT GTCAGACCAA GTTTACTCAT ATATACTTTA GATTGATTTA AAACTTCATT
2041 TTTAATTTAA AAGGATCTAG GTGAAGATCC TTTTTGATAA TCTCATGACC AAAATCCCTT
2101 AACGTGAGTT TTCGTTCCAC TGAGCGTCAG ACCCCGTAGA AAAGATCAAA GGATCTTCTT
2161 GAGATCCTTT TTTTCTGCGC GTAATCTGCT GCTTGCAAAC AAAAAAACCA CCGCTACCAG
2221 CGGTGGTTTG TTTGCCGGAT CAAGAGCTAC CAACTCTTTT TCCGAAGGTA ACTGGCTTCA
2281 GCAGAGCGCA GATACCAAAT ACTGTCCTTC TAGTGTAGCC GTAGTTAGGC CACCACTTCA
2341 AGAACTCTGT AGCACCGCCT ACATACCTCG CTCTGCTAAT CCTGTTACCA GTGGCTGCTG
2401 CCAGTGGCGA TAAGTCGTGT CTTACCGGGT TGGACTCAAG ACGATAGTTA CCGGATAAGG
2461 CGCAGCGGTC GGGCTGAACG GGGGGTTCGT GCACACAGCC CAGCTTGGAG CGAACGACCT
2521 ACACCGAACT GAGATACCTA CAGCGTGAGC ATTGAGAAAG CGCCACGCTT CCCGAAGGGA
2581 GAAAGGCGGA CAGGTATCCG GTAAGCGGCA GGGTCGGAAC AGGAGAGCGC ACGAGGGAGC
2641 TTCCAGGGGG AAACGCCTGG TATCTTTATA GTCCTGTCGG GTTTCGCCAC CTCTGACTTG
2701 AGCGTCGATT TTTGTGATGC TCGTCAGGGG GGCGGAGCCT ATGGAAAAAC GCCAGCAACG
2761 CGGCCTTTTT ACGGTTCCTG GCCTTTTGCT GGCCTTTTGC TCACATGTTC TTTCCTGCGT
2821 TATCCCCTGA TTCTGTGGAT AACCGTATTA CCGCCTTTGA GTGAGCTGAT ACCGCTCGCC
2881 GCAGCCGAAC GACCGAGCGC AGCGAGTCAG TGAGCGAGGA AGCGGAAG
```

TERMINATION CODON OF β-LACTAMASE

FIG. 5

```
EcoR I    10         20         30         40         50         60
GAATTCATGGGTCTGTCTGACGGTCTGACGGTGCAGCTGGTTCTGAACGTTTGGGGTAAAGTT
         MetGlyLeuSerAspGlyLeuThrValGlnLeuValLeuAsnValTrpGlyLysVal
         INITIATION CODON
          70         80         90        100        110        120
GAAGCTGACATCCCGGGTCATGGTCAGGAAGTTCTGATCCGTCTGTTTAAAGGTCATCCG
GluAlaAspIleProGlyHisGlyGlnGluValLeuIleArgLeuPheLysGlyHisPro
         130        140        150        160        170        180
GAAACCCTGGAAAAGTTCGATAAATTTAAACATCTGAAATCTGAAGACGAAATGAAAGCT
GluThrLeuGluLysPheAspLysPheLysHisLeuLysSerGluAspGluMetLysAla
         190        200        210        220        230        240
TCTGAAGACCTGAAAAAACATGGTGCTACCGTTCTGACCGTTGGCTGGCATCCTGAAA
SerGluAspLeuLysLysHisGlyAlaThrValLeuThrValAlaLeuGlyGlyIleLeuLeuLys
         250        260        270        280        290        300
AAGAAAGGTCATCATGAAGCTGAAATCAAACCGCTGGCTCAGTCTCATGCTACCAAACAT
LysLysGlyHisHisGluAlaGluIleLysProLeuAlaGlnSerHisAlaThrLysHis
         310        320        330        340        350        360
AAAATCCCGGTTAAATATCTGGAATTATCTCTGAATGCATCATCCAGGTTCTGCAGTCT
LysIleProValLysTyrLeuGluPheIleSerGluCysIleIleIleGlnValLeuGlnSer
         370        380        390        400        410        420
AAACATCCGGGTGACTTTGGTGCTGACGGTCAGGGTGCTATGAACAAAGCTCTGGAACTG
LysHisProGlyAspPheGlyAlaAspAlaGlyAlaAlaMetAsnLysAlaLeuGluLeu
         430        440        450        460        470        480
TTTCGTAAAGACATGGCTTCTAACTATAAAGAACTGGGTTTTCAGGGTTGATAAGGATCC
PheArgLysAspMetAlaSerAsnTyrLysGluLeuGlyPheGlnGly*****BamHI
                                                  TERMINATION CODON
```

FIG. 6

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 484 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
CCGAATTCAT  GGGTCTGTCT  GACGGTGAAT  GGCAGCTGGT  TCTGAACGTT  TGGGGTAAAG      60

TTGAAGCTGA  CATCCCGGGT  CATGGTCAGG  AAGTTCTGAT  CCGTCTGTTT  AAAGGTCATC     120

CGGAAACCCT  GGAAAAGTTC  GATAAATTTA  AACATCTGAA  ATCTGAAGAC  GAAATGAAAG     180

CTTCTGAAGA  CCTGAAAAAA  CATGGTGCTA  CCGTTCTGAC  CGCTCTGGGT  GGCATCCTGA     240

AAAAGAAAGG  TCATCATGAA  GCTGAAATCA  AACCGCTGGC  TCAGTCTCAT  GCTACCAAAC     300
```

| ATAAAATCCC | GGTTAAATAT | CTGGAATTTA | TCTCTGAATG | CATCATCCAG | GTTCTGCAGT | 360 |
| CTAAACATCC | GGGTGACTTT | GGTGCTGACG | CTCAGGGTGC | TATGAACAAA | GCTCTGGAAC | 420 |
| TGTTTCGTAA | AGACATGGCT | TCTAACTATA | AGAACTGGG  | TTTTCAGGGT | TGATAAGGAT | 480 |
| CCGG | | | | | | 484 |

(2) INFORMATION FOR SEQ ID NO:2:

(i) SEQUENCE CHARACTERISTICS:
        (A) LENGTH: 2928 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:2:

| AGCGCCCAAT | ACGCAAACCG | CCTCTCCCCG | CGCGTTGGCC | GATTCATTAA | TGCAGCTGGC | 60 |
| ACGACAGGTT | TCCCGACTGG | AAAGCGGGCA | GTGAGCGCAA | CGCAATTAAT | GTGAGTTAGC | 120 |
| TCACTCATTA | GCCACCCCAG | GCTTTACACT | TTATGCTTCC | GGCTCGTATG | TTGTGTGGAA | 180 |
| TTGTGAGCGG | ATAACAATTT | CACACAGGAA | ACAGCTATGA | CCATGATTAC | GCCAAGCTCT | 240 |
| AATACGACTC | ACTATAGGGA | AAGCTTCCCT | GTTGACAATT | AATCATCGAA | CTAGTTAACT | 300 |
| AGTACGCAAG | TTCACGTAAA | AAGGGTAGAA | TTCGAGCTCG | GTACCCGGGG | ATCCTCTAGA | 360 |
| GTCGACCTGC | AGGTCGAAAT | TCACTGGCCG | TCGTTTTACA | ACGTCGTGAC | TGGGAAAACC | 420 |
| CTGGCGTTAC | CCAACTTAAT | CGCCTTGCAG | CACATCCCCC | TTTCGCCAGC | TGGCGTAATA | 480 |
| GCGAAGAGGC | CCGCACCGAT | CGCCCTTCCC | AACAGTTGCG | CAGCCTGAAT | GGCGAATGGG | 540 |
| ACGCGCCCTG | TAGCGGCGCA | TTAAGCGCGG | CGGGTGTGGT | GGTTACGCGC | AGCGTGACCG | 600 |
| CTACACTTGC | CAGCGCCCTA | CCGCCCGCTC | CTTTCGCTTT | CTTCCCTTCC | TTTCTCGCCA | 660 |
| CGTTCGCCGG | CTTTCCCCGT | CAAGCTCTAA | ATCGGGGGCT | CCCTTTAGGG | TTCCGATTTA | 720 |
| GTGCTTTACG | GCACCTCGAC | CCCAAAAAAC | TTGATTAGGG | TGATGGTTCA | CGTAGTGGGC | 780 |
| CATCGCCCTG | ATAGACGGTT | TTTCGCCCTT | TGACGTTGGA | GTCCACGTTC | TTTAATAGTG | 840 |
| GACTCTTGTT | CCAAACTGGA | ACAACACTCA | ACCCTATCTC | GGTCTATTCT | TTTGATTTAT | 900 |
| AAGGGATTTT | GCCGATTTCG | GCCTATTGGT | TAAAAAATGA | GCTGATTTAA | CAAAAATTTA | 960 |
| ACGCGAATTT | TAACAAAATA | TTAACGTTTA | CAATTTCAGG | TGGCACTTTT | CGGGGAAATG | 1020 |
| TGCCCGGAAC | CCCTATTTGT | TTATTTTTCT | AAATACATTC | AAATATGTAT | CCGCTCATGA | 1080 |
| GACAATAACC | CTGATAAATG | CTTCAATAAT | ATTGAAAAAG | GAAGAGTATG | AGTATTCAAC | 1140 |
| ATTTCCGTGT | CGCCCTTATT | CCCTTTTTTG | CGGCATTTTG | CCTTCCTGTT | TTTGCTCACC | 1200 |
| CAGAAACGCT | GGTGAAACTA | AAAGATGCTG | AAGATCAGTT | GGGTGCACGA | GTGGGTTACA | 1260 |
| TCGAACTGGA | TCTCAACAGC | GGTAAGATCC | TTGAGAGTTT | TCGCCCCGAA | GAACGTTTTC | 1320 |
| CAATGATGAC | CACTTTTAAA | GTTCTGCTAT | GTGGCGCGGT | ATTATCCCGT | ATTGACGCCG | 1380 |
| GGCAAGAGCA | ACTCGGTCGC | CGCATACACT | ATTCTCAGAA | TGACTTGGTT | GAGTACTCAC | 1440 |
| CAGTCACAGA | AAAGCATCTT | ACGGATGGCA | TGACAGTAAG | AGAATTATGC | AGTGCTGCCA | 1500 |
| TAACCATGAG | TGATAACACT | GCGGCCAACT | TACTTCTGAC | AACGATCGGA | GGACCGAAGG | 1560 |
| AGCTAACCGC | TTTTTTGCAC | AACATGGGGG | ATCATGTAAC | TCGCCTTGAT | CGTTGGGAAC | 1620 |
| CGGAGCTGAA | TGAAGCCATA | CCAAACGACG | AGCGTGACAC | CACGATGCCT | GTAGCAATGG | 1680 |
| CAACAACGTT | GCGCAAACTA | TTAACTGGCG | AACTACTTAC | TCTAGCTTCC | CGGCAACAAT | 1740 |
| TAATAGACTG | GATGGAGGCG | GATAAAGTTG | CAGGACCACT | TCTGCGCTCG | GCCCTTCCGG | 1800 |

-continued

```
CTGGCTGGTT TATTGCTGAT AAATCTGGAG CCGGTGAGCG TGGGTCTCGC GGTATCATTG   1860
CAGCACTGGG GCCAGATGGT AAGCCCTCCC GTATCGTAGT TATCTACACG ACGGGGAGTC   1920
AGGCAACTAT GGATGAACGA AATAGACAGA TCGCTGAGAT AGGTGCCTCA CTGATTAAGC   1980
ATTGCTAACT GTCAGACCAA GTTTACTCAT ATATACTTTA GATTGATTTA AAACTTCATT   2040
TTTAATTTAA AAGGATCTAG GTGAAGATCC TTTTTGATAA TCTCATGACC AAAATCCCTT   2100
AACGTGAGTT TTCGTTCCAC TGAGCGTCAG ACCCCGTAGA AAAGATCAAA GGATCTTCTT   2160
GAGATCCTTT TTTTCTGCGC GTAATCTGCT GCTTGCAAAC AAAAAAACCA CCGCTACCAG   2220
CGGTGGTTTG TTTGCCGGAT CAAGAGCTAC CAACTCTTTT TCCGAAGGTA ACTGGCTTCA   2280
GCAGAGCGCA GATACCAAAT ACTGTCCTTC TAGTGTAGCC GTAGTTAGGC CACCACTTCA   2340
AGAACTCTGT AGCACCGCCT ACATACCTCG CTCTGCTAAT CCTGTTACCA GTGGCTGCTG   2400
CCAGTGGCGA TAAGTCGTGT CTTACCGGGT TGGACTCAAG ACGATAGTTA CCGGATAACG   2460
CGCAGCGGTC GGGCTGAACG GGGGGTTCGT GCACACAGCC CAGCTTGGAG CGAACGACCT   2520
ACACCGAACT GAGATACCTA CAGCGTGAGC ATTGAGAAAG CGCCACGCTT CCCGAAGGGA   2580
GAAAGGCGGA CAGGTATCCG GTAAGCGGCA GGGTCGGAAC AGGAGAGCGC ACGAGGGAGC   2640
TTCCAGGGGG AAACGCCTGG TATCTTTATA GTCCTGTCGG GTTTCGCCAC CTCTGACTTG   2700
AGCGTCGATT TTTGTGATGC TCGTCAGGGG GGCGGAGCCT ATGGAAAAAC GCCAGCAACG   2760
CGGCCTTTTT ACGGTTCCTG GCCTTTTGCT GGCCTTTTGC TCACATGTTC TTTCCTGCGT   2820
TATCCCCTGA TTCTGTGGAT AACCGTATTA CCGCCTTTGA GTGAGCTGAT ACCGCTCGCC   2880
GCAGCCGAAC GACCGAGCGC AGCGAGTCAG TGAGCGAGGA AGCGGAAG             2928
```

( 2 ) INFORMATION FOR SEQ ID NO:3:

( i ) SEQUENCE CHARACTERISTICS:
        ( A ) LENGTH: 480 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 7..469

( x i ) SEQUENCE DESCRIPTION: SEQ ID NO:3:

```
GAATTC ATG GGT CTG TCT GAC GGT GAA TGG CAG CTG CTT CTG AAC GTT          48
       Met Gly Leu Ser Asp Gly Glu Trp Gln Leu Leu Leu Asn Val
        1               5                  10

TGG GGT AAA GTT GAA GCT GAC ATC CCC CGT CAT CCT CAC CAA CTT CTC         96
Trp Gly Lys Val Glu Ala Asp Ile Pro Arg His Pro His Gln Leu Leu
 15                  20                  25                  30

ATC CCT CTC TTT AAA GGT CAT CCG GAA ACC CTG CAA AAG TTC GAT AAA        144
Ile Pro Leu Phe Lys Gly His Pro Glu Thr Leu Gln Lys Phe Asp Lys
                 35                  40                  45

TTT AAA CAT CTG AAA TCT GAA GAC GAA ATG AAA GCT TCT GAA GAC CTG        192
Phe Lys His Leu Lys Ser Glu Asp Glu Met Lys Ala Ser Glu Asp Leu
             50                  55                  60

AAA AAA CAT GGT GCT ACC GTT CTG ACC GCT CTG GGT GGC ATC CTG AAA        240
Lys Lys His Gly Ala Thr Val Leu Thr Ala Leu Gly Gly Ile Leu Lys
         65                  70                  75

AAG AAA GGT CAT CAT GAA GCT GAA ATC AAA CCG CTG GCT CAG TCT CAT        288
Lys Lys Gly His His Glu Ala Glu Ile Lys Pro Leu Ala Gln Ser His
     80                  85                  90
```

-continued

| | | | | | | | | | | | | | | | | |
|---|---|---|---|---|---|---|---|---|---|---|---|---|---|---|---|---|
| GCT | ACC | AAA | CAT | AAA | ATC | CCG | GTT | AAA | TAT | CTG | GAA | TTT | ATC | TCT | GAA | 336 |
| Ala | Thr | Lys | His | Lys | Ile | Pro | Val | Lys | Tyr | Leu | Glu | Phe | Ile | Ser | Glu | |
| 95 | | | | | 100 | | | | | 105 | | | | | 110 | |
| TGC | ATC | ATC | CAG | GTT | CTG | CAG | TCT | AAA | CAT | CCG | GGT | GAC | TTT | GGT | GCT | 384 |
| Cys | Ile | Ile | Gln | Val | Leu | Gln | Ser | Lys | His | Pro | Gly | Asp | Phe | Gly | Ala | |
| | | | | 115 | | | | | 120 | | | | | 125 | | |
| GAC | GCT | CAG | GGT | GCT | ATG | AAC | AAA | GCT | CTG | GAA | CTG | TTT | CGT | AAA | GAC | 432 |
| Asp | Ala | Gln | Gly | Ala | Met | Asn | Lys | Ala | Leu | Glu | Leu | Phe | Arg | Lys | Asp | |
| | | | 130 | | | | | 135 | | | | | 140 | | | |
| ATG | GCT | TCT | AAC | TAT | AAA | GAA | CTG | GGT | TTT | CAG | GGT | T | GATAAGGATC | | | 479 |
| Met | Ala | Ser | Asn | Tyr | Lys | Glu | Leu | Gly | Phe | Gln | Gly | | | | | |
| | | 145 | | | | | 150 | | | | | | | | | |
| C | | | | | | | | | | | | | | | | 480 |

( 2 ) INFORMATION FOR SEQ ID NO:4:

( i ) SEQUENCE CHARACTERISTICS:
        ( A ) LENGTH: 154 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

| Met | Gly | Leu | Ser | Asp | Gly | Glu | Trp | Gln | Leu | Leu | Leu | Asn | Val | Trp | Gly |
|---|---|---|---|---|---|---|---|---|---|---|---|---|---|---|---|
| 1 | | | | 5 | | | | | 10 | | | | | 15 | |
| Lys | Val | Glu | Ala | Asp | Ile | Pro | Arg | His | Pro | His | Gln | Leu | Leu | Ile | Pro |
| | | | 20 | | | | | 25 | | | | | 30 | | |
| Leu | Phe | Lys | Gly | His | Pro | Glu | Thr | Leu | Gln | Lys | Phe | Asp | Lys | Phe | Lys |
| | | 35 | | | | | 40 | | | | | 45 | | | |
| His | Leu | Lys | Ser | Glu | Asp | Glu | Met | Lys | Ala | Ser | Glu | Asp | Leu | Lys | Lys |
| | 50 | | | | | 55 | | | | | 60 | | | | |
| His | Gly | Ala | Thr | Val | Leu | Thr | Ala | Leu | Gly | Gly | Ile | Leu | Lys | Lys | Lys |
| 65 | | | | | 70 | | | | | 75 | | | | | 80 |
| Gly | His | His | Glu | Ala | Glu | Ile | Lys | Pro | Leu | Ala | Gln | Ser | His | Ala | Thr |
| | | | | 85 | | | | | 90 | | | | | 95 | |
| Lys | His | Lys | Ile | Pro | Val | Lys | Tyr | Leu | Glu | Phe | Ile | Ser | Glu | Cys | Ile |
| | | | 100 | | | | | 105 | | | | | 110 | | |
| Ile | Gln | Val | Leu | Gln | Ser | Lys | His | Pro | Gly | Asp | Phe | Gly | Ala | Asp | Ala |
| | | 115 | | | | | 120 | | | | | 125 | | | |
| Gln | Gly | Ala | Met | Asn | Lys | Ala | Leu | Glu | Leu | Phe | Arg | Lys | Asp | Met | Ala |
| | | 130 | | | | | 135 | | | | | 140 | | | |
| Ser | Asn | Tyr | Lys | Glu | Leu | Gly | Phe | Gln | Gly | | | | | | |
| 145 | | | | | 150 | | | | | | | | | | |

METHOD FOR PRODUCING RECOMBINANT HUMAN MYOGLOBIN

DETAILED DESCRIPTION OF THE INVENTION

1. Field of the Invention

The present invention relates to production of human myoglobin having a molecular weight of 17,600. More precisely, it relates to production of myoglobin by designing a DNA sequence of such a gene of myoglobin as can be efficiently produced in microorganisms such as cells of *E. coli*, artificially synthesizing the gene, introducing the gene in cells of *E. coli* and separating and purifying myoglobin from the cells.

The myoglobin to be obtained according to the present invention is useful as a laboratory reagent for medicochemistry, biochemistry and pharmacy and is especially worthy of being utilized as an antigen for preparing an antibody for a myoglobin test in a clinical examination and as a calibrator for the test.

2. Prior Art

Myoglobin is a hemoprotein containing one protoheme, which functions as a carrier of storing oxygen in the muscular tissue in living organisms. There are known some reports referring to the expression of myoglobin in microorganisms (yeast, *E. coli*, etc.). In one report referring to the expression of human myoglobin in *E. coli* (Varadarajan, R., Szabo, A., Boxer, S.G., (1985) Proc. Natl. Acad. Sci., USA, 82, 5681–5684), the myoglobin was expressed as a heme-free apo-myoglobin. There has heretofore been disclosed no report demonstrating the expression and production of a holo-type human myoglobin in *E. coli*.

Problems to be Solved by the Invention:

As mentioned hereinabove, where a recombinant human myoglobin was expressed in *Escherichia coli* (*E. coli*), it was expressed only as an apo-protein but was not as a holo-protein that actually exists in living organisms. According to the prior art technique, therefore, it was impossible to obtain a human myoglobin of a holo-type protein unless the myoglobin produced in the cells was once separated and purified from the cells and thereafter it was reconstructed to have a heme-type structure.

The separation and purification of myoglobin itself, which shall be conducted for converting the myoglobin produced by the prior art technique into a holo-type protein, is not easy and, in addition, the prior art technique needs the operation for reconstructing the thus-isolated myoglobin to make it have a heme-type structure. This reconstructing operation is disadvantageous especially in mass-production on an industrial scale. Therefore, it is desired in this technical field, especially from the viewpoint of industrial production of myoglobin, to develop a method for directly producing a holo-type myoglobin by expressing it as a holo-type protein in the cells of microorganisms.

In view of the current situation of the related technique as mentioned hereinabove, the object of the present invention is to develop a system of producing human myoglobin on an industrial scale by modifying an expression system of *E. coli* and expressing human myoglobin as a heme-structured holo-protein in the cells of *E. coli* with the modified expression system.

BRIEF DESCRIPTION OF THE DRAWINGS

FIG. 4 shows the latter part of the base sequence (SEQ ID NO:2) of the foregoing expression vector.

MEANS FOR SOLVING THE PROBLEMS

The present invention has been made in order to attain the above-mentioned object. As a result of various investigations, we, the present inventors have found a method for making *E. coli* efficiently express a heme-structured holo-type human myoglobin. On the basis of this finding, we have completed the present invention realizing the production of human myoglobin on an industrial scale.

Figure 5:
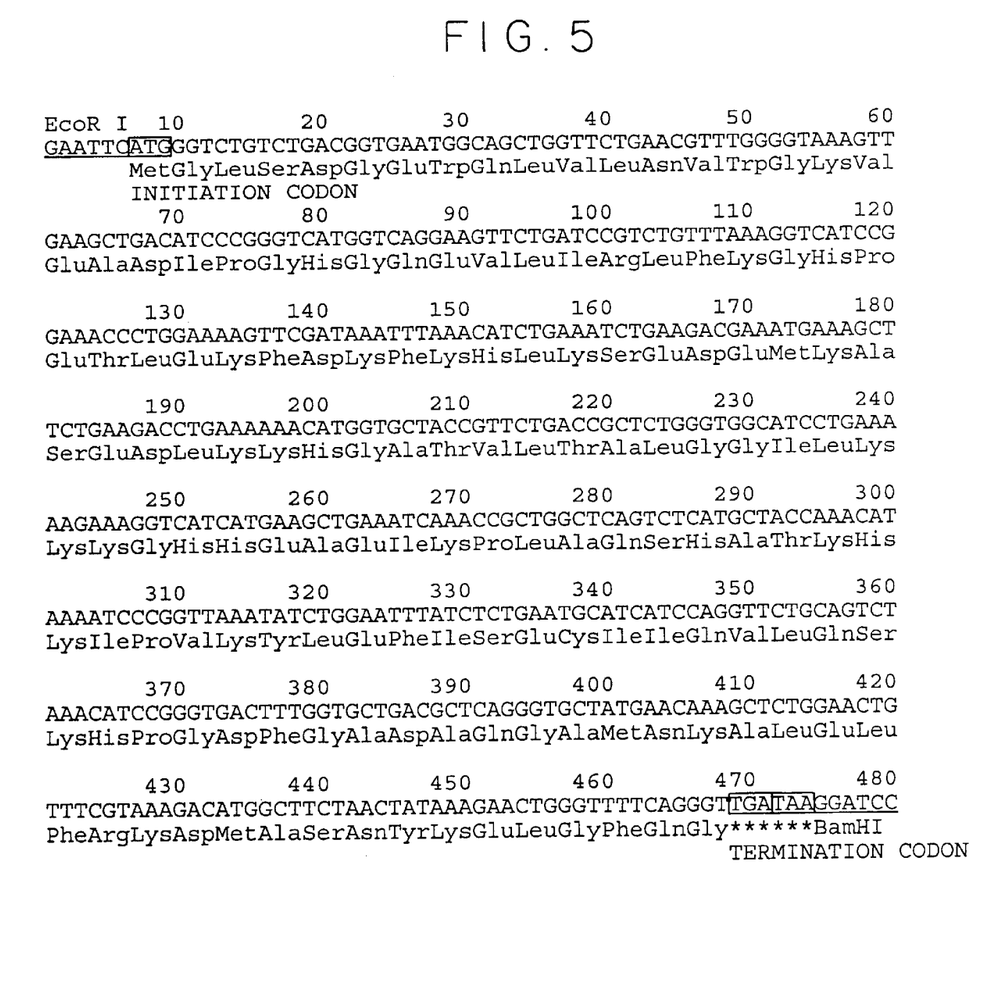
FIG. 5 shows the base sequence (SEQ ID NO:1) and the amino acid sequence (SEQ ID NO:4) of the structural gene of human myoglobin.
Figure 6:
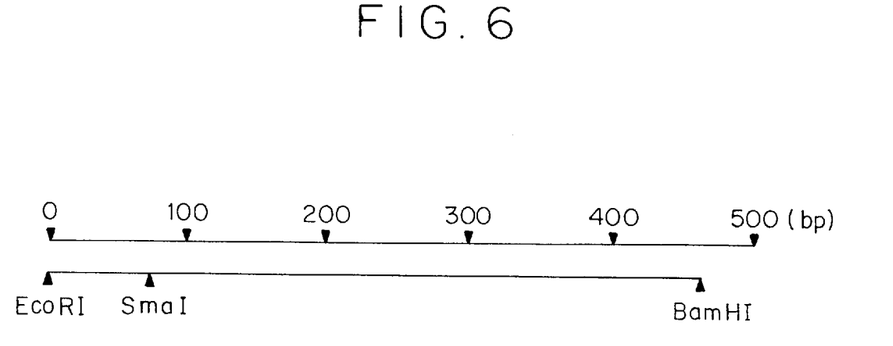
FIG. 6 shows a restriction endonuclease map of the human myoglobin gene.

The method for producing human myoglobin of the present invention is described herein under. The DNA sequence of human myoglobin has already been known (Akaboshi, E., (1985), Gene, 33, 241–249). The structural gene and the amino acid sequence of human myoglobin are shown in FIG. 5, and the restriction endonuclease map thereof is in FIG. 6.

However, even if the human myoglobin gene is desired to be expressed in *Escherichia coli* (*E. coli*), the expression efficiency is generally low. In addition, even though the human myoglobin gene is expressed in *E. coli*, a holo-type myoglobin cannot be obtained, as so mentioned hereinabove.

A DNA sequence of human myoglobin gene has been designed, using optimum codons for *E. coli*, in order to make *E. coli* directly and efficiently express a holo-type myoglobin. In addition, restriction endonuclease sites (EcoRI-BamHI) have been linked to the both ends of the sequence for cloning the gene to thereby make the gene have a full length of 484 base pairs. This human myoglobin gene (with 484 base pairs) has been prepared by chemical synthesis. This has been inserted into an expression vector (pTRP vector) for use in the present invention, with which the cells of *E. coli* JM109 (TAKARA) have been transformed. The thus-transformed cells of *E. coli* have been incubated at 37° C. for 16 hours and then disrupted, and the myoglobin produced in the cytoplasm has been confirmed and identified by physico-chemical means and immunological means.

We, the present inventors, having provided the present invention, have succeeded not only in designing and actually constructing the synthetic gene containing the sequence of human myoglobin gene but also in efficiently expressing the synthetic gene which is especially difficult to express by variously modifying and improving the gene recombination technique for the expression. In addition, the present invention is the first to have realized the industrial production of a holo-type human myoglobin that could not be obtained by the conventional gene recombination technique. Next, the present invention is described in more detail by means of the following example.

EXAMPLE 1

(1) Designing of human myoglobin gene

Figure 1:
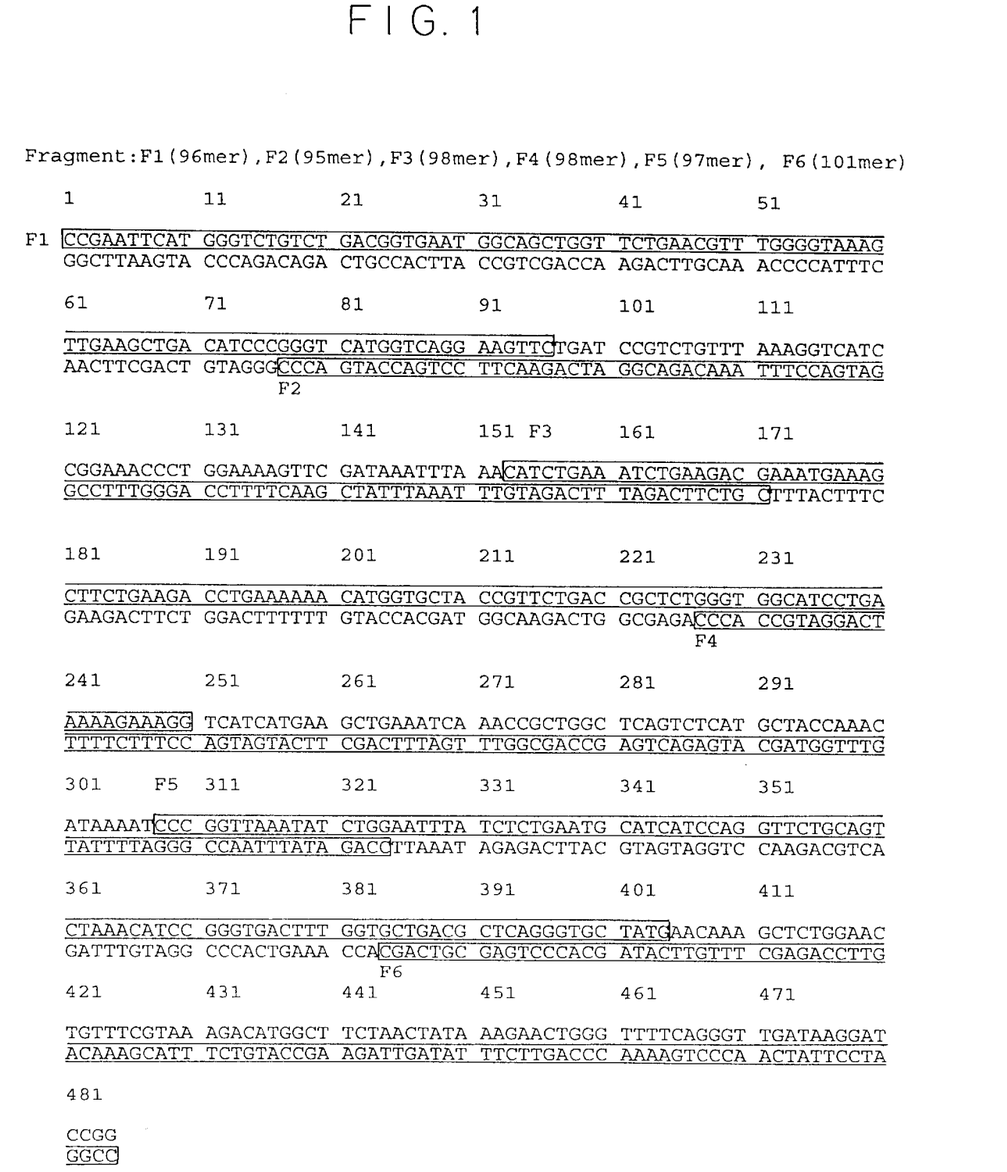
FIG. 1 shows the base sequence (SEQ ID NO:1) of the recombinant human myoglobin gene designed by the present invention.

A DNA sequence of human myoglobin was designed, using optimum codons for *E. coli*, in order to make *E. coli* efficiently express the human myoglobin (FIG. 1). Next, recognition sequences of EcoRI and BamHI were introduced into the N-terminal end and the C-terminal end of the sequence, respectively, in order to insert the gene sequence into an expression vector, thereby making the gene have a full length of 484 base pairs.

The DNA sequence of the resulting human myoglobin gene is shown hereinunder as SEQ ID NO:1 in the Sequence Listing.

Figure 2:
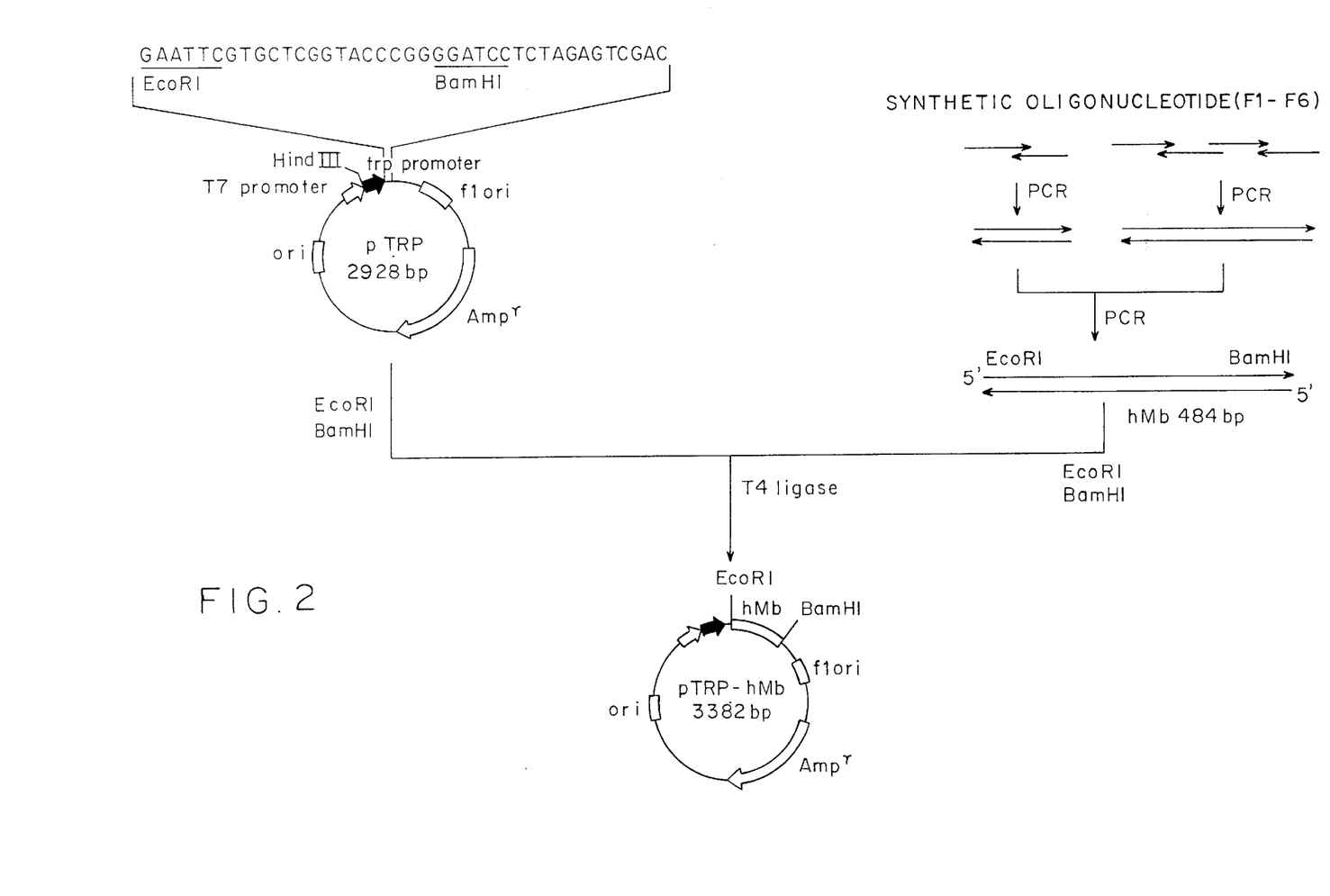
FIG. 2 shows the construction of an expression plasmid for the present invention.
Figure 3:
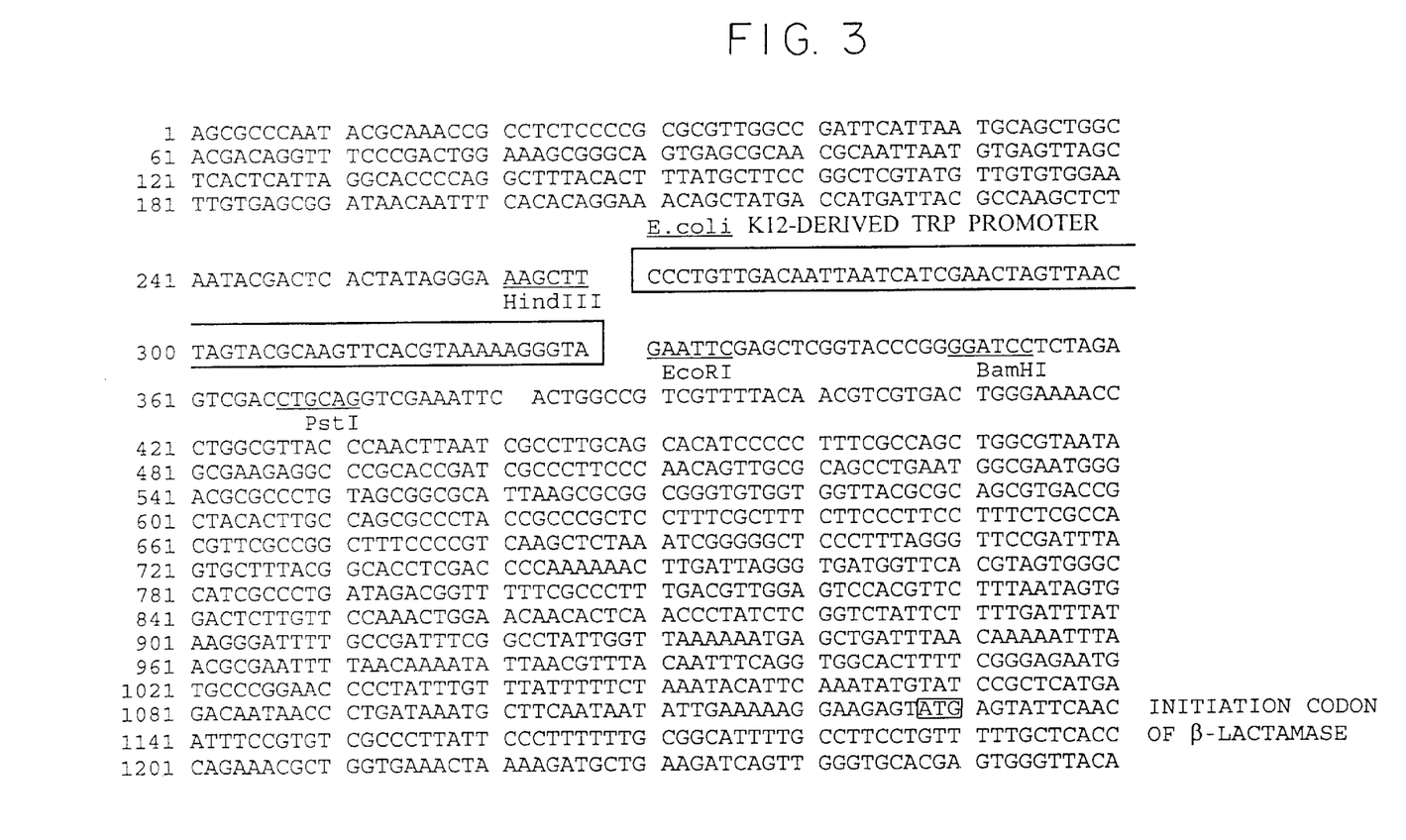
FIG. 3 shows the former part of the base sequence (SEQ ID NO:2) (full-length base sequence with 2928 bp) of an expression vector pTRP used in the present invention.

(2) Construction of a plasmid with which *E. coli* is made to express the human myoglobin The human myoglobin having restriction endonuclease recognition sequences of EcoRI and BamHI added thereto and having a full gene length of 484 base pairs was cut into six oligonucleotides (F1 to F6) each having a length of about 95 bases (FIG. 1). These were synthesized, using an automatic DNA synthesizer. From these, obtained was a full-length gene by PCR according to the process shown in FIG. 2. As the expression vector, used was a pTRP vector having a tryptophan promoter (FIG. 3, FIG. 4). This expression vector was cut with EcoRI and BamHI, and the synthetic gene of human myoglobin was inserted thereinto to form a plasmid pTRP-hMb. The ligation was conducted with a T4 DNA ligase, at 16° C. for 2 hours. Cells of *E. coli* JM109 were transformed with the resulting reaction product. The plasmid of the resulting transformants was isolated by alkali-SDS method. The plasmid was cut with the restriction enzymes whereby the insertion of the intended gene into the plasmid was confirmed. Cells of *E. coli* JM109 were again transformed with the plasmid.

*Escherichia coli* JM109 that had been transformed with the plasmid pTRP-hMb was referred to as *Escherichia coli* JM109/pTRP-hMb. *Escherichia coli* JM109/pTRP-hMb has been deposited in the National Institute of Bioscience and Human-Technology Agency of Industrial Science and Technology 1-3, Higashi 1-chome, Tsukuba-shi, Ibaraki-ken, 305, Japan, on Oct. 5, 1994, and assigned accession/deposit number FERM P-14575. This deposit was subsequently designated as an international deposit under the Budapest Treaty on Jul. 28, 1995, with the same depository and assigned accession/deposit number FERM BP-5181.

(3) Incubation of transformant cells

The cells of *E. coli* JM109 (FERM BP-5181) that had been transformed with the plasmid pTRP-hMb were incubated in an LB medium containing 125 µg/ml of ampicillin, at 30° C. for 16 hours. The resulting culture was inoculated on an LB medium containing 125 µg/ml of ampicillin, at a concentration of 3%, and then incubated at 37° C. for 10 hours.

(4) Purification of myoglobin and properties thereof

After having been incubated at 37° C., the cells expressed a soluble, matured myoglobin of 17.5K in their cytoplasms. The cells were suspended in 50 mM Tris-HCl (pH 8.5) buffer containing 1 mM of EDTA of from 3 to 5 times by volume of the cells. The cells in the suspension were disrupted with a Dyno mill. The resulting suspension was then subjected to centrifugation at 10,000 rpm for 30 minutes at 4° C., by which the supernatant was separated from the precipitate. After the supernatant was passed through a DEAE-cellulose column to thereby remove protein impurities therefrom to some extent, it was subjected to ion-exchange chromatography with Q-Sepharose big beads (Pharmacia). The essential fraction resulting from this chromatography was finally purified by isoelectric point electrophoresis (isoelectric focusing) to obtain a pure human myoglobin giving a single band in SDS-PAGE with CBBR staining.

Advantages of the Invention

According to the present invention, it has become possible to easily carry out mass-production of a heme-structured, holo-type myoglobin with cells of *E. coli*, which, however, has heretofore been impossible by the prior art technique.

What is claimed is:

1. A recombinant gene encoding for human myoglobin, comprising a sequence of SEQ ID NO:1.

2. A plasmid comprising the recombinant gene according to claim 1 and a tryptophan promoter.

3. An *Escherichia coli* host cell transformed with the plasmid according to claim 2.

4. A method for producing a human heme-structured, holo-myoglobin, comprising the steps of:
culturing the transformed *Escherichia coli* host cell of claim 3 to express and produce a human heme-structured holo-myoglobin; and
recovering the expressed and produced human heme-structured holo-myoglobin.

5. The plasmid according to claim 2, which is prepared by the steps of:
digesting pTRP vector comprising SEQ ID NO:3 with EcoRI and BamHI; and
inserting the recombinant gene encoding for human myoglobin comprising a sequence of SEQ ID NO:1 into the EcoRI and BamHI-digested PTRP vector.

6. An *Escherichia coli* host cell transformed with the plasmid according to claim 5.

7. A method for producing a human heme-structured, holo-myoglobin, comprising the steps of:
culturing the transformed *Escherichia coli* host cell of claim 5 to express and produce a human heme-structured holo-myoglobin; and
recovering the expressed and produced human heme-structured holo-myoglobin.

8. The plasmid according to claim 2, wherein the plasmid is pTRP-hMb.

9. An *Escherichia coli* host cell transformed with the plasmid according to claim 8.

10. The transformed *Escherichia coli* host cell according to claim 8 which is *Escherichia coli* JP109/pTRP-hMb, deposited with the National Institute of Bioscience and Human-Technology in Japan under the accession/deposit number FERM BP-5181.

11. A method for producing a human heme-structured, holo-myoglobin, comprising the steps of:
  culturing the transformed *Escherichia coli* host cell of claim 8 to express and produce a human heme-structured holo-myoglobin; and
  recovering the expressed and produced human heme-structured holo-myoglobin.

* * * * *